United States Patent
An (10) Patent No.: US 10,441,220 B2
(45) Date of Patent: Oct. 15, 2019

(54) WEARABLE LIQUID CRYSTAL DISPLAY USING BIO-SIGNAL, AND CONTROL METHOD THEREOF

(71) Applicant: Samsung Display Co., Ltd., Yongin-si, Gyeonggi-do (KR)

(72) Inventor: Min Su An, Hwaseong-si (KR)

(73) Assignee: Samsung Display Co., Ltd. (KR)

( * ) Notice: Subject to any disclaimer, the term of this patent is extended or adjusted under 35 U.S.C. 154(b) by 438 days.

(21) Appl. No.: 15/072,177

(22) Filed: Mar. 16, 2016

(65) Prior Publication Data

US 2017/0071541 A1 Mar. 16, 2017

(30) Foreign Application Priority Data

Sep. 11, 2015 (KR) .................. 10-2015-0129115

(51) Int. Cl.
- *A61B 5/022* (2006.01)
- *A61B 5/00* (2006.01)
- *A61B 5/107* (2006.01)
- *A61B 5/1171* (2016.01)

(52) U.S. Cl.
CPC .......... *A61B 5/6844* (2013.01); *A61B 5/0002* (2013.01); *A61B 5/1072* (2013.01); *A61B 5/1171* (2016.02); *A61B 5/681* (2013.01); *A61B 5/742* (2013.01); *A61B 5/7475* (2013.01); *A61B 2560/0475* (2013.01)

(58) Field of Classification Search
CPC ......... A61B 5/00; A61B 5/024; A61B 5/0245; A61B 5/1455; A61B 5/02416; A61B 5/02444; A61B 5/14552; A61B 5/681; A61B 5/02438; A61B 5/0404; G04G 21/025
USPC ........................................ 600/499
See application file for complete search history.

(56) References Cited

U.S. PATENT DOCUMENTS

| | | | | |
|---|---|---|---|---|
| 2014/0089673 | A1* | 3/2014 | Luna | H04L 63/0861 713/186 |
| 2016/0287103 | A1* | 10/2016 | Saponas | A61B 5/02233 |

FOREIGN PATENT DOCUMENTS

| | | |
|---|---|---|
| KR | 10-0674869 B1 | 1/2007 |
| KR | 10-2009-0043709 A | 5/2009 |
| KR | 10-2014-0064687 A | 5/2014 |
| KR | 10-2015-0029105 A | 3/2015 |
| KR | 10-2015-0039325 A | 4/2015 |

* cited by examiner

*Primary Examiner* — Jon Eric C Morales
(74) *Attorney, Agent, or Firm* — Innovation Counsel LLP (57) ABSTRACT

The present disclosure relates to a wearable display device. According to an exemplary embodiment, the wearable display device includes: a display unit configured to display an image; a wearing means configured to fix the display unit on a body part; a plurality of sensors positioned on one surface of the wearing means and configured to contact a measuring target to measure a bio-signal from the measuring target; and a wearing means adjustment section included in the display unit and configured to adjust a length of the wearing means contacting the measuring target of the wearing means by using the bio-signal.

8 Claims, 10 Drawing Sheets

WEARABLE LIQUID CRYSTAL DISPLAY USING BIO-SIGNAL, AND CONTROL METHOD THEREOF

CROSS-REFERENCE TO RELATED APPLICATION

This application claims priority to and the benefit of Korean Patent Application No. 10-2015-0129115 filed in the Korean Intellectual Property Office on Sep. 11, 2015, the entire contents of which are incorporated herein by reference.

BACKGROUND (a) Technical Field

The present disclosure relates to a wearable display device and a control method thereof, and in detail, relates to a wearable display device controlling a function by using a bio-signal and a control method thereof.

(b) Description of the Related Art

A flat panel display generally includes a liquid crystal display (LCD), an organic light emitting diode display (OLED display), an electrophoretic display, a plasma display, and the like. The flat panel display includes a plurality of pairs of electric field generating electrodes and an electro-optical active layer. A liquid crystal display includes a liquid crystal layer as the electro-optical active layer, and an organic light emitting display includes an organic light emitting layer as the electro-optical active layer. One of the electric field generating electrodes forming a pair is usually connected to a switching element and receives an electrical signal, and the electro-optical active layer converts the electrical signal into an optical signal, thereby displaying an image.

The liquid crystal display has been variously developed in aspects of usage, form, size, etc., and is actively used in a wearable mobile device.

Recently, with the proliferation of smart devices, the emergence of wearable mobile devices having new and various forms is accelerated.

The mobile device provides a number of conveniences to the lives of modern people. As the computing power of mobile devices grows, the users are more able to perform a lot of work that was performed by PCs etc., by using the mobile devices. As mobile devices are widely used, protection of personal information, such as a telephone number, a photograph, a personal multimedia content such as a motion picture, mail, financial relation information, that are stored in the devices becomes important. When the user loses the mobile device, or an unspecified user randomly uses the mobile device, the personal information is susceptible to misuse against the user's intent. Accordingly, a method capable of controlling certification of the user that wishes to use the mobile device and access to various personal information stored to the mobile device is required.

Also, automation technology related to the function and the operation of the wearable mobile device has been continually developed.

The above information disclosed in this Background section is only for enhancement of understanding of the background of the disclosure and therefore may contain information that does not form the prior art that is already known in this country to a person of ordinary skill in the art.

SUMMARY

The present disclosure provides a method of controlling the operation of the wearable display device using a user bio-signal and performing user certification by using the bio-signal, and a device thereof.

A wearable display device according to an exemplary embodiment of the present disclosure includes: a display unit configured to display an image; a wearing means configured to fix the display unit on a body part; a plurality of sensors positioned on one surface of the wearing means and configured to contact a measuring target to measure a bio-signal from the measuring target; and a wearing means adjustment section included in the display unit and configured to adjust a length of the wearing means contacting the measuring target of the wearing means by using the bio-signal.

The wearing means may further include at least one motor positioned at a connection part of the wearing means and the display unit and configured to be driven for adjustment of the length of the wearing means.

The display unit may further include a memory configured to store at least one information which directly or indirectly expresses the bio-signal.

The display unit may further include a wearing means adjustment section configured to determine the length of the wearing means reflecting a body characteristic of the measuring target by using the bio-signal. At least some of the plurality of sensors may be configured to sense a first bio-signal generated by a user gesture, and the wearing means adjustment section may be configured to compare the first bio-signal with a wear reference value stored in the memory to determine the length of the wearing means. The wearing means adjustment section may be configured to generate a control signal including a signal on the length of the wearing means and transmit the control signal to the motor.

At least some of the plurality of sensors may be configured to measure a second bio-signal from the measuring target after the driving of the motor for adjusting the length of the wearing means is completed.

The display unit may further include a certification section configured to derive at least one of user certification information on the basis of the second bio-signal and store the at least one of user certification information in the memory.

The user certification information may include at least one selected from a wrist thickness and a wrist length of the measuring target when the wearable display device is worn on a wrist of the measuring target.

At least some of the plurality of sensors may be configured to measure the second bio-signals at different positions with a predetermined interval between the different positions for the measuring target depending on the user gesture, and the certification section may be configured to derive at least one selected from the wrist thickness and the wrist length of the measuring target on the basis of the second bio-signals at the different positions.

At least some of the plurality of sensors may be configured to measure a third bio-signal from the measuring target in a state in which the length of the wearing means is adjusted, and the certification section may be configured to perform a user certification procedure by determining whether the third bio-signal corresponds to the user certification information stored in the memory.

A method for controlling a wearable display device according to an exemplary embodiment of the present disclosure including a display unit, a wearing means fixing the display unit on a body part, a plurality of sensors contacting the measuring target and measuring a bio-signal from the measuring target, and a motor driven for length adjustment of the wearing means, the method includes: measuring a first bio-signal by at least some of the plurality of sensors, the first bio-signal generated in response to the wearable display device being worn on the body part; and adjusting a length of the wearing means contacting the measuring target of the wearing means on the basis of the first bio-signal.

The step of adjusting the length of the wearing means may include: comparing the first bio-signal and a predetermined wear reference value stored in the memory to determine the length of the wearing means by the display unit; generating a control signal including a signal on the length of the wearing means and transmitting the control signal to the motor by the display unit; and driving the motor to adjust the length of the wearing means depending on the control signal.

The method may further include measuring a second bio-signal from the measuring target by at least some of the plurality of sensors after adjusting the length of the wearing means.

The method may further include deriving at least one of the user certification information on the basis of the second bio-signal and storing the at least one of user certification information in the memory, wherein the user certification information may include at least one selected from a wrist thickness and a wrist length information of the measuring target when the wearable display device is worn on a wrist of the measuring target.

The step of storing the user certification information may include: measuring the second bio-signals at different positions with a predetermined interval between the different positions for the measuring target depending on the user gesture by the at least some of the plurality of sensors; and deriving at least one selected from the wrist thickness and the wrist length information of the measuring target on the basis of the second bio-signals at the different positions.

The method may further include: adjusting the length of the wearing means after storing the user certification information; measuring a third bio-signal from the measuring target by the at least some of the plurality of sensors in a state in which the length of the wearing means is adjusted; and determining whether the third bio-signal corresponds to the user certification information stored in the memory to perform a user certification procedure.

In the user certification procedure, the user certification procedure may be performed by considering a predetermined error range when comparing the third bio-signal and the user certification information stored in the memory.

When the user is certified, the method may further include providing a user interface depending on a setting information of the display device for the certified user with reference to the memory.

When the user is not certified, the method may further include: controlling the display unit so as to end a device operation in the display device.

According to an exemplary embodiment of the present disclosure, by controlling the certification and the operation of the wearable display device by using the bio-signal, user convenience may be increased and leakage of personal information may be prevented.

DETAILED DESCRIPTION OF THE EMBODIMENTS

Exemplary embodiments of the present disclosure are described in detail with reference to the attached drawings. The present disclosure may be modified in many different forms, and should not be construed as being limited to the exemplary embodiments set forth herein. Rather, the exemplary embodiments of the present disclosure are provided to help convey the concept of the present disclosure to those skilled in the art.

Figure 1:
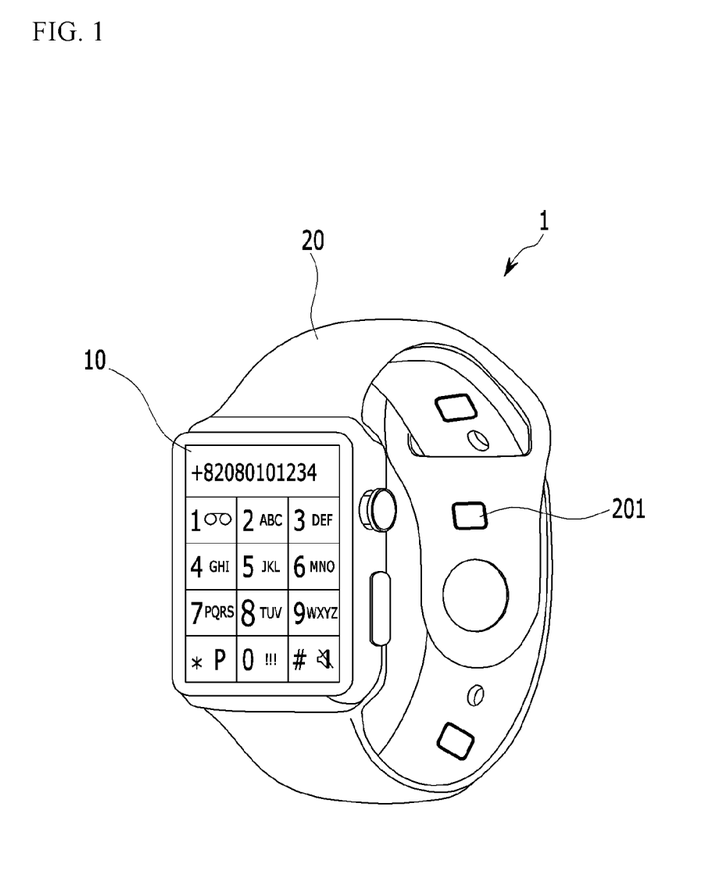
FIG. 1 is a view showing one example of a wearable display device according to an exemplary embodiment of the present disclosure.
Figure 2A:
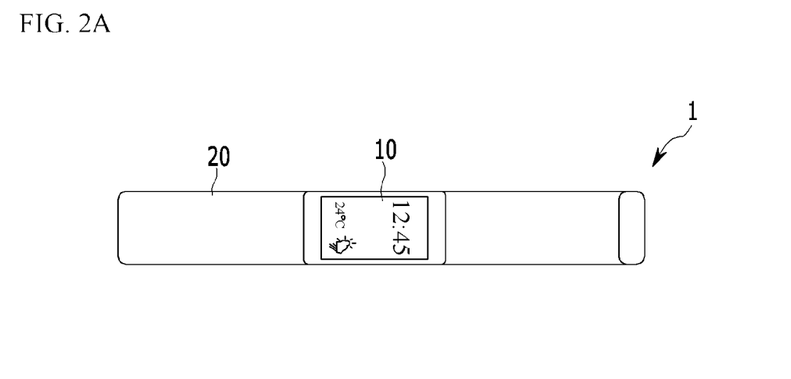
FIGS. 2A, 2B and 2C are cross-sectional views showing one example of a front surface, a back surface, and a side surface of the wearable display device shown in FIG. 1.
Figure 2B:
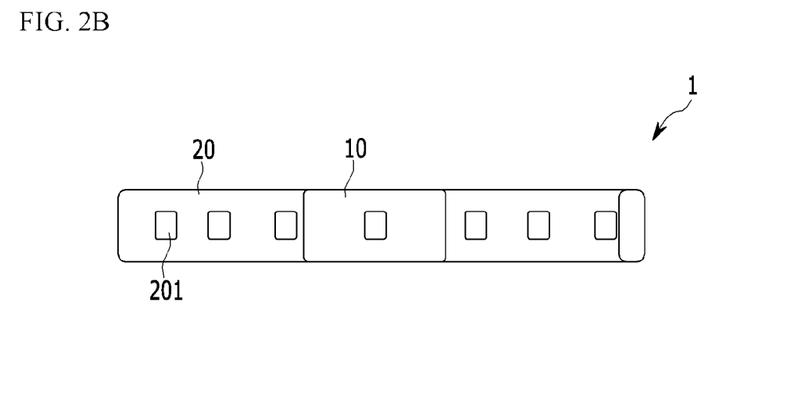
Figure 2C:
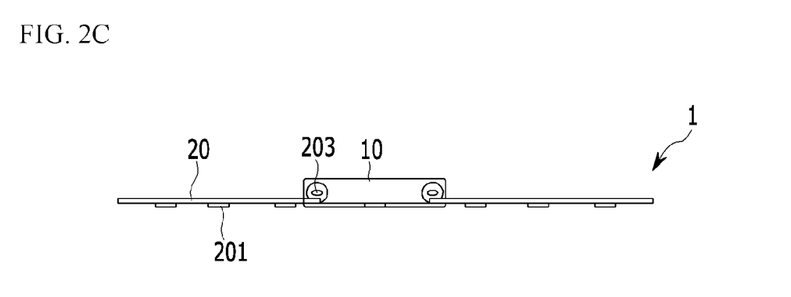

FIG. 1 is a view showing one example of a wearable display device according to an exemplary embodiment of the present disclosure. FIG. 2 is a cross-sectional view showing one example of a front surface, a back surface, and a side surface of the wearable display device shown in FIG. 1.

Referring to FIG. 1 and FIG. 2, a wearable display device 1 according to an exemplary embodiment of the present disclosure is worn on the body of the user to contact a measuring target. For example, the wearable display device 1 may be attachable, wearable, or detachable with respect to a body part, such as by using an arm band, a wrist band, or other fixing devices.

The wearable display device 1 includes a display unit 10 outputting an image or a video that the user can see and a wearing means 20 to wear the display unit 10 to the body part. Referring to FIGS. 2A and 2B, the wearing means 20 may be divided into 'a front surface' that is exposed outside when worn and 'a back surface' that contacts the body of the user, and a plurality of sensors 201 are positioned in the back surface of the wearing means 20.

The plurality of sensor 201 measures a user bio-signal from the user when the user is wearing the wearable display device 1 and therefore contacting the sensor 201.

For example, when wearing the wearable display device 1, the user may open a hand, hold a fist, or twist a wrist as a predetermined gesture and thereby generate a trigger signal. Hereafter, in the present specification, when the user is wearing the wearable display device 1, the bio-signal measured by the sensor 201 due to the trigger signal is referred to as 'a first bio-signal'. For better comprehension and ease of description, the trigger signal and the first bio-signal are divided, and as the user generates the predetermined gesture when wearing the wearable display device 1, the bio-signal measured by the sensor 201 may be the trigger signal and simultaneously may be the first bio-signal. Also, when the user is wearing the wearable display device 1, and the sensor 201 recognizes the wearing state, even if the user does not perform the predetermined gesture, the first bio-signal may be measured in the present worn state.

The sensor 201 measures the first bio-signal to be transmitted to the display unit 10, and the display unit 10 may determine a wearing means length that is suitable for the body characteristic, such as a user wrist size, by using the first bio-signal.

Referring to FIG. 2C, a motor 203 to adjust the wearing means length is positioned at both sides of the display unit 10 that are connected with the wearing means 20. The motors 203 at both sides of the display unit 10 are driven to adjust the wearing means length so as to meet the wearing means length determined on the basis of the first bio-signal when the user wears the wearable display device 1.

Next, if the length of the wearing means 20 is adjusted on the basis of the user body characteristic, at least some of the plurality of sensors 201 positioned at the wearing means 20 are operated to again measure the user bio-signal. Next, in the present specification, the bio-signal that is again measured when the wearing means length is adjusted to be suitable for the user body characteristic is referred to as 'a second bio-signal'.

The display unit 10 starts a user certification procedure on the basis of the second bio-signal.

Figure 3:
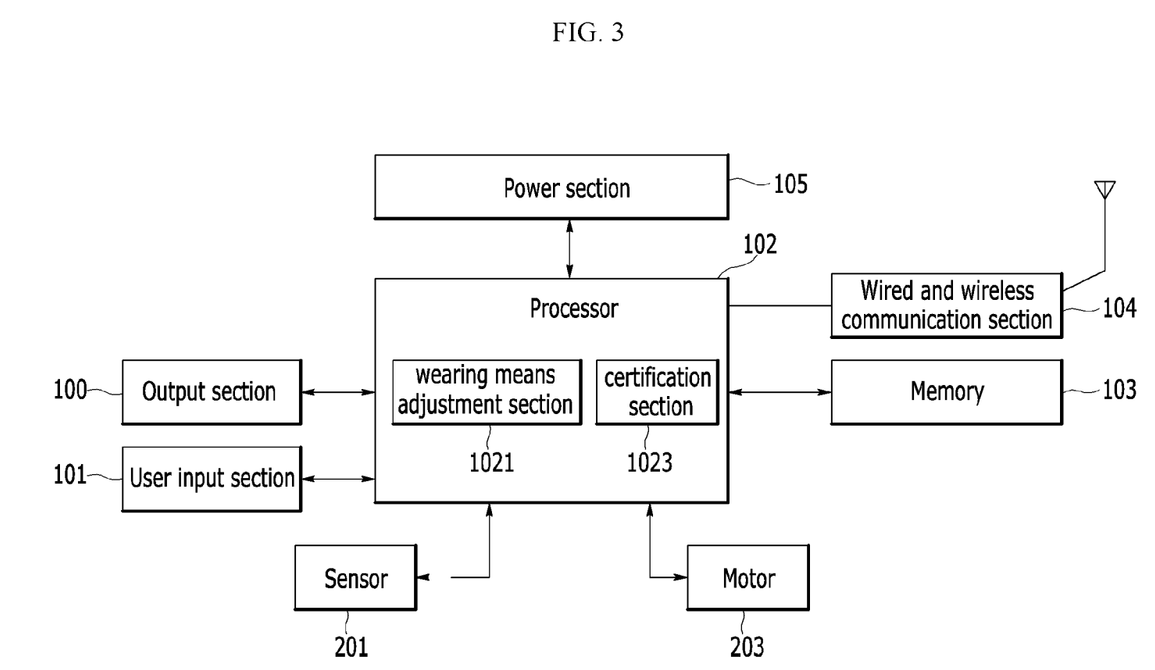
FIG. 3 is a block diagram of one example of a wearable display device according to an exemplary embodiment of the present disclosure.

FIG. 3 is a view showing an example of a block diagram of a wearable display device according to an exemplary embodiment of the present disclosure.

Referring to FIG. 3, the wearable display device 1 according to an exemplary embodiment of the present disclosure may include an output section 100, a user input section 101, a processor 102, a memory 103, a wired and wireless communication section 104, and a power section 105 in a display unit 10, and a plurality of sensors 201 and a motor 203 positioned in the wearing means 20. The processor 102 may further include a wearing means adjustment section 1021 to adjust the length of the wearing means 20 and a certification section 1023 for the user certification. For better comprehension and ease of description, an exemplary embodiment in which the sensor 201 uses a pressure sensor is described.

Next, each configuration of the wearable display device 1 is described.

The output section 100 as a display device displaying an image may use a flat panel display such as a liquid crystal display (LCD), an organic light emitting diode (OLED) display, an electrophoretic display, and a plasma display.

The output section 100 may output data analyzing the bio-signal measured by the sensor 201, data transmitted from external communication equipment through the wired and wireless communication section 104, and information provided from the display unit 10. Also, output section 100 may include the function of the user input section 101 capable of inputting the signal by the user.

The output section 100 is described later with reference to FIG. 9 and FIG. 10.

The user input section 101 inputs the signal depending on the user to the processor 102 to operate the function depending on the corresponding signal, and the output section 100 may become the user input section 101. For example, as the image data output, like the touch screen, and the input means, like the user interface, are simultaneously provided, the user input section 101 and the output section 100 may be the same configuration. The user may set, change, or release a wearing means length adjustment function, a user certification related function, and a report function of a lost device on the basis of the certification result through the user input section 101.

The processor 102 controls each element of the wearable display device 1, including its operations. Also, the processor 102 may further include the wearing means adjustment section 1021 to control the wearing means 20, such as the wearing means length optimized for each user on the basis of the user bio-signal, and the certification section 1023 performing the user certification information registration and the certification procedure.

The wearing means adjustment section 1021 adjusts the length of the wearing means 20 on the basis of a wear reference value pre-stored to the memory 103 using at least some of the plurality of sensors 201. The wear reference value may be information that directly or indirectly expresses the bio-signal stored at the memory 103

In the present specification, 'the wear reference value' may be defined as a bio-signal value that may be measured by the sensor 201 when the user optimally wears the wearable display device 1. For example, when the sensor 201 is a pressure sensor, 'the wear reference value may be set as the pressure value measured by the pressure sensor in the state that the length of the wearing means 20 is adjusted to feel a sense of stability and comfort while the user wears the wearable display device 1. The wear reference value may be automatically pre-set or registered and changed by the user through the user input section 101.

The wearing means adjustment section 1021 compares the first bio-signal measured in the sensor 201 and the wear reference value stored in the memory 103 to determine the optimized wearing means length. The optimized wearing means length is determined for each user, and the wearing means adjustment section 1021 transmits the control signal related to the wearing means length adjustment to the motor 203.

If the length of the wearing means 20 is controlled as the optimized length on the basis of the user body characteristic, at least some of the plurality of sensors 201 may measure the second bio-signal.

The certification section 1023 analyzes the second bio-signal measured in the sensor 201 to perform the user certification information registration for the wearable display device 1 and the certification procedure for the wearing user. 'User certification information' may be defined as a reference bio-signal registered to the certification section 1023 to identify the user, and may include the user body characteristic (for example, a thickness or a length of the wrist, etc.) derived from the analysis result of the second bio-signal.

Also, the certification section 1023 may perform the user certification procedure by a method of comparing the user certification information and the third bio-signal measured in the sensor 201 according to the further re-wearing of the wearable display device for the user. In the present specification, 'the third bio-signal' may be defined as the bio-signal that is re-measured when the wearing means length is adjusted to be suitable for the user body characteristic after the user certification information registration for better comprehension and ease of description.

Also, the processor 102 may control the driving of the wearable display device 1 on the basis of the user certification result.

When the user is certified, the processor 102 may drive the wearable display device 1, read the device setting information of the certified user with reference to the memory 103, and provide the user interface on the basis of the device setting information. Also, when the user certification has failed a predetermined number of times or more, the processor 102 may stop the operation of the wearable display device 1 and drive it to be registered as a lost device.

In the memory 103, access information for at least one function that may be executable in the wearable display device 1 is stored. For example, a function of deriving medical data by analyzing the bio-signal, or various functions such as financial services, personal mail, Internet usage, and SMS transmission may be executed, and each function may require different access rights. The memory 103 may store the access information corresponding to the various functions to be executable in the wearable display device 1.

The wired and wireless communication section 104 allows the wearable display device 1 to be connected to an external device by a wired or wireless channel to perform data communication. The wired and wireless communication section 104 may receive the data from the external device, depending on the usage and the function of the wearable display device 1, or may transmit the data generated in the wearable display device 1.

The sensor 201 includes the plurality of sensors to measure the bio-signal of the measuring target, and may use the pressure sensor measuring blood pressure or a pulse, a temperature sensor, such as a thermistor measuring body temperature, a displacement sensor measuring the pulse, or an approximate displacement.

According to an exemplary embodiment, for the sensor 201, the plurality of sensors may be arranged with a predetermined interval or positioned appropriately to measure the bio-signal on the back surface of the wearing means 20.

The sensor 201 measures the first bio-signal when a predetermined condition is met in the state in which the user wears the wearable display device 1, and measures the second bio-signal or the third bio-signal after the wearing means 20 length is adjusted depending on the user body characteristic. The second bio-signal or the third bio-signal is re-measured as the pressure sensor of the sensor 201 contacts the user body surface and may be more accurate compared with the first bio-signal.

The motor 203 is driven to adjust the length of the wearing means 20 connected to the motor 203 on the basis of the control signal of the wearing means adjustment section 1021.

Figure 4:
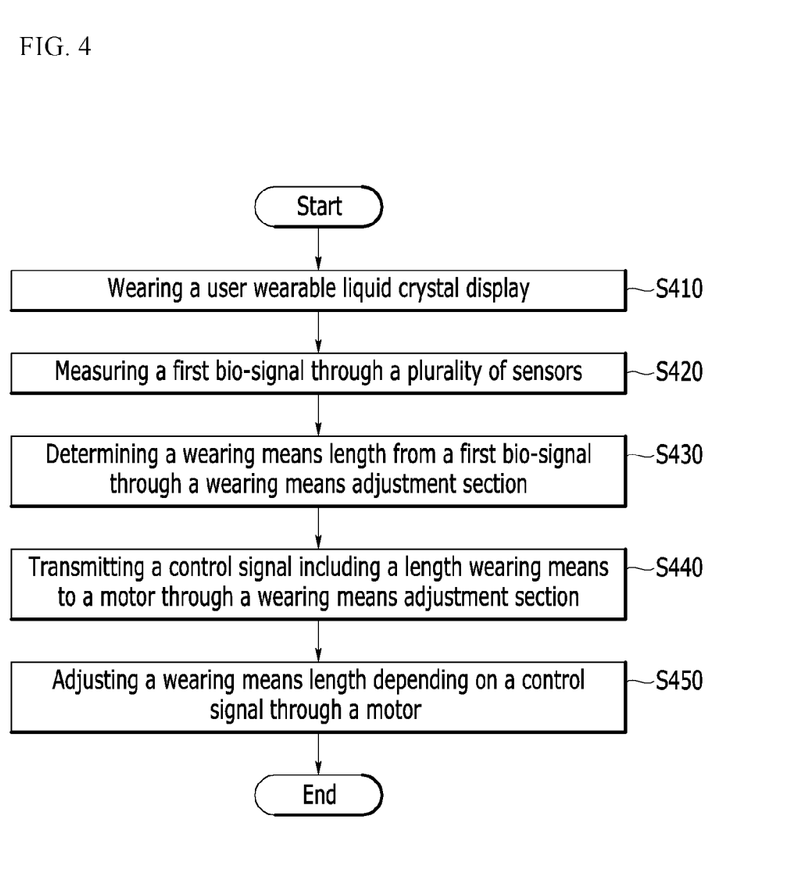
FIG. 4 is a procedure flowchart to explain one example of a procedure for automatically controlling a wearing means length of a wearable display device according to an exemplary embodiment of the present disclosure.
Figure 5A:
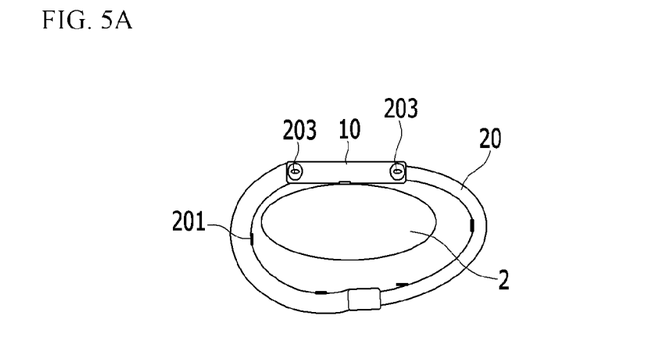
FIGS. 5A, 5B and 5C are views showing one example of a driving process of the wearable display device according to the exemplary embodiment of FIG. 4.
Figure 5B:
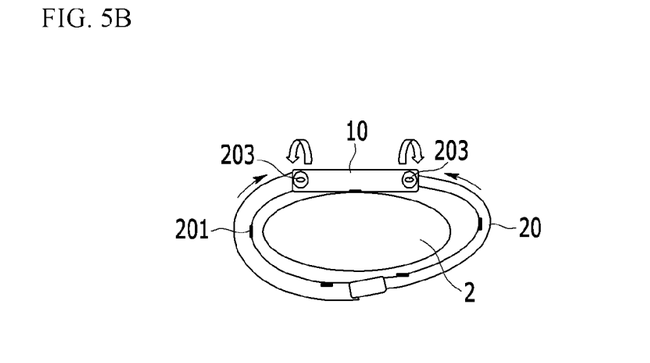
Figure 5C:
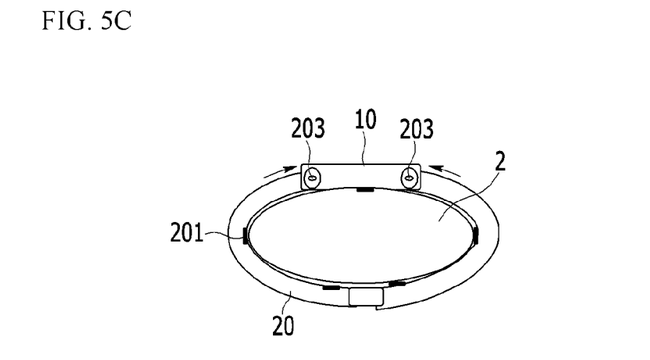

FIG. 4 is a procedure flowchart to explain one example of a procedure for automatically controlling a wearing means length of a wearable display device according to an exemplary embodiment of the present disclosure. FIG. 5 is a view showing one example of a driving process of the wearable display device according to the exemplary embodiment of FIG. 4.

Referring to FIG. 4, the user wears the wearable display device 1 on the body part 2, and as shown FIG. 5A, the part of the wearable display device 1 may not contact the body part 2 (S410).

If the trigger signal is generated after the user wears the wearable display device 1, at least some of the sensors 201 positioned with the predetermined interval on the back surface of the wearing means 20 measures the first bio-signal for the wearing user (S420). The first bio-signal may be the same as the trigger signal, or a signal indicating whether the wearable display device 1 is being worn by the user as the bio-signal measured after the trigger signal.

The wearing means adjustment section 1021 derives the wear reference value stored to the memory 103 on the basis of the first bio-signal, and compares it with the first bio-signal to determine the wearing means length optimized for the user (S430).

Also, the wearing means adjustment section 1021 transmits the control signal for the optimized wearing means length to the motor 203 connected to the wearing means 20 (S440).

As shown in FIG. 5B, the motor 203 is driven to adjust the length of the wearing means 20 on the basis of the control signal (S450). That is, the motor 203 may perform the operation of winding the wearing means in the display unit 10 until the length of the wearing means 20 reaches the wearing means length included in the control signal transmitted from the wearing means adjustment section 1021.

Accordingly, as shown in FIG. 5C, the user may wear the wearable display device 1 more close-fittingly over the body part 2 without a separate operation of the wearable display device 1.

Figure 6:
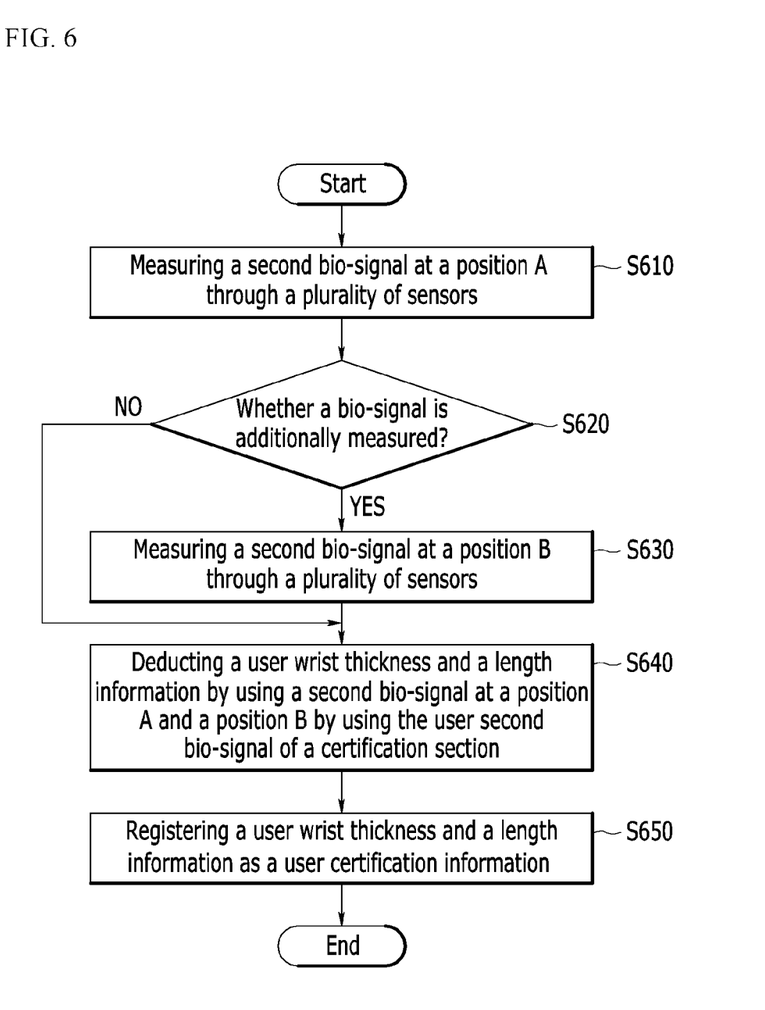
FIG. 6 is a procedure flowchart to explain one example of user certification information registration of a wearable display device according to an exemplary embodiment of the present disclosure.
Figure 7:
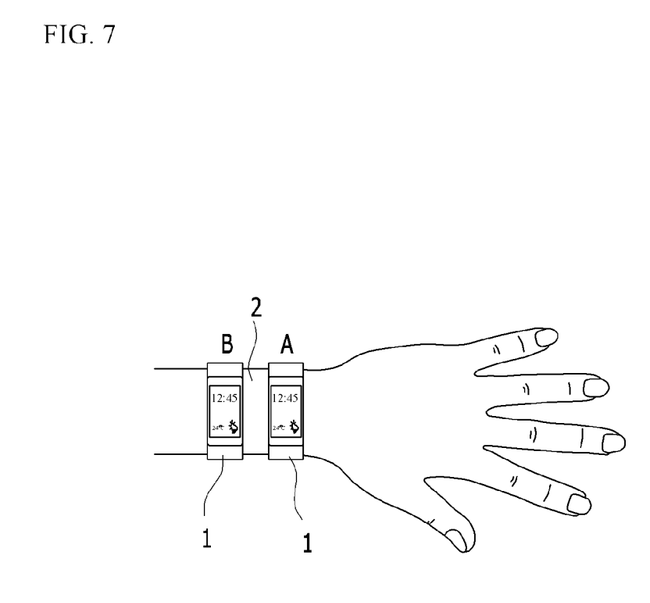
FIG. 7 is a view showing one example of wearing a wearable display device for the user certification information registration of FIG. 6.

FIG. 6 is a procedure flowchart to explain one example of user certification information registration of a wearable display device according to an exemplary embodiment of the present disclosure. FIG. 7 is a view showing one example of wearing a wearable display device for the user certification information registration of FIG. 6. In this case, for better comprehension and ease of description, as the user wears the wearable display device 1, the process of adjusting the length of the wearing means 20 so that the wearing state is optimized for the user body part 2 is omitted.

Referring to FIG. 6, as the user wears the wearable display device 1 at a position A of the body, at least some of the plurality of sensors 201 positioned at the wearing means 20 measure the user second bio-signal at the position A (S610).

In this case, in the process of the registration of the user certification information, the user may register the user certification information by using the second bio-signal measured by a one-time wearing or by using the second bio-signal measured by wearing several times.

That is, the wearable display device 1 may perform a verification procedure for accuracy of the user certification information according to the user selection signal through the user input section 101 in the registration of the user certification information (S620).

According to the user selection signal, the user re-wears the wearable display device 1 at the position B of the body (see FIG. 7), and at least some of the plurality of sensors 201 measures the user second bio-signal at the position B (S630).

For example, when the user wears the wearable display device 1 on the wrist in a form of bracelets or watches, as shown in FIG. 7, the wearable display device 1 may measure the second bio-signal two times or more at the position A (see FIG. 7) and the position B while wearing the wearable display device 1 on the wrist with the predetermined interval. Also, although not shown in FIG. 6, the process of re-measuring the user second bio-signal may be repeated several times.

The certification section 1023 obtains the user wrist thickness and the length information from the position A to the position B by using the user second bio-signal of the position and the user second bio-signal of the position B (S640).

Next, the user certification information is registered by using the user wrist thickness and length information from the position A to the position B (S640). In this case, the certification section 1023 may set an error range to be acceptable between the second bio-signal measured in the sensor 201 and the user certification information stored in the memory 103, and the predetermined error range may be set or changed through the user input section 101.

The user certification information may be transmitted through the wired and wireless communication section 104 to an external communication device or a management server remotely managing the wearable display device 1, or may be stored in the memory 103 to be used for the certification procedure in the future.

Figure 8:
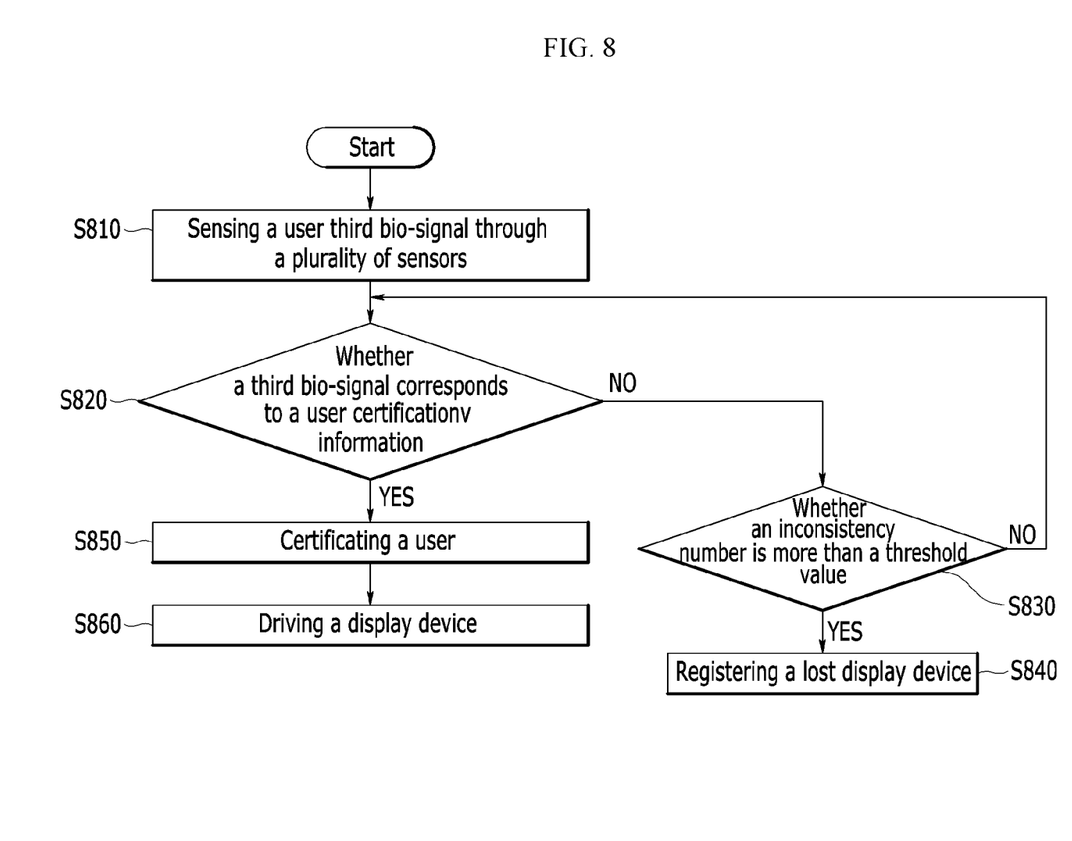
FIG. 8 is a procedure flowchart to explain one example of a user certification procedure of a wearable display device according to an exemplary embodiment of the present disclosure.

FIG. 8 is a procedure flowchart to explain one example of a user certification procedure of a wearable display device according to an exemplary embodiment of the present disclosure. Likewise, for better comprehension and ease of description, as the user wears the wearable display device 1, the process of adjusting the length of the wearing means 20 to be the wearing state optimized for the user body 2 for the wearing means 20 is omitted.

Referring to FIG. 8, as the user wears the wearable display device 1 on the body part, at least some of the plurality of sensors 201 positioned on the wearing means 20 measures the user third bio-signal (S810).

The certification section 1023 determines whether the user third bio-signal corresponds to the user certification information stored in the memory 103 (S820).

If it is determined that the third bio-signal does not correspond to the user certification information stored in the memory in the step S820, the processor 102 may control the device operation to be ended.

In this case, to re-perform the user certification procedure, the procedure is returned to the step S810 and the second bio-signal is re-measured until the predetermined certification confirmation number is reached, and the procedure determining whether the second bio-signal corresponds to the user certification information in the step S820 may be repeated (S830). The certification confirmation number may be changed depending on the user input.

When the user certification verification procedure corresponds to the predetermined certification confirmation number, the processor 102 may register the wearable display device 1 as a lost device (S840). When the certification procedure has failed, the function of registering as the lost device may be set and released by the user through the user input section 101.

If the third bio-signal corresponds to the user certification information stored in the memory 103 in the step S820, the processor 102 may certify the user (S850).

When the user is certified according to the exemplary embodiment, the wearable display device 1 may read the device setting information of the certified user with reference to the memory 103 and may provide the user interface according to the device setting information. In this case, the device setting information respectively corresponding to at least one user may be stored to the memory 103 of the wearable display device 1.

Figure 9:
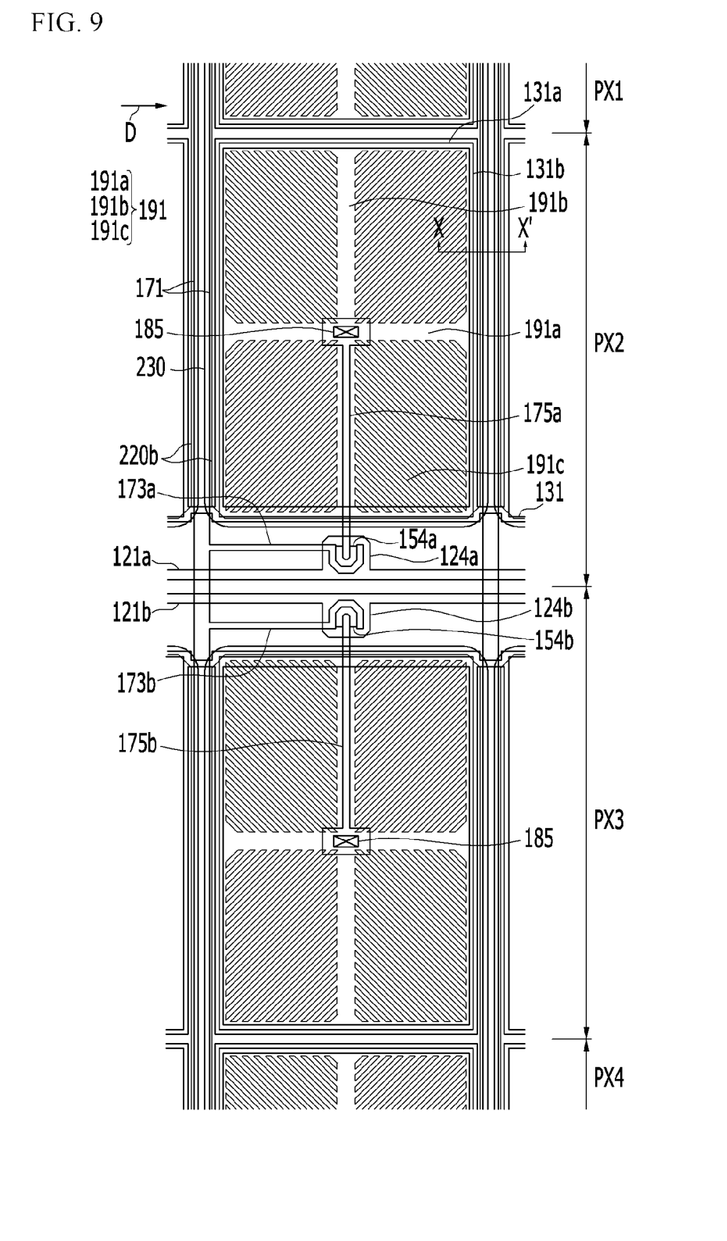
FIG. 9 is a layout view showing a part of a pixel of a wearable display device according to an exemplary embodiment of the present disclosure.

FIG. 9 is a layout view showing a part of a pixel of a wearable display device according to an exemplary embodiment of the present disclosure. FIG. 10 is a cross-sectional view of the liquid crystal display of FIG. 9 taken along a line X-X'.

Referring to FIG. 9, in the output section 100 of the wearable liquid crystal display 1, a first gate line 121a, a second gate line 121b, and a storage electrode line 131 are formed on a substrate 110 made of transparent glass or plastic. The first gate line 121a and the second gate line 121b are positioned as a pair between two pairs of pixels PX1 and PX2, and PX3 and PX4.

The first gate line 121a and the second gate line 121b transmit a gate signal and extend substantially in the transverse direction. The first gate line 121a includes a first gate electrode 124a, and the second gate line 121b includes a second gate electrode 124b.

The storage electrode line 131 transmits a predetermined voltage such as a common voltage Vcom, and includes a' longitudinal portion 131b extending substantially perpendicular to the first gate line 121a and the second gate line 121b and a transverse portion 131a connected to an end of the longitudinal portion 131b.

A data line 171 transmits a data signal and extends in the longitudinal direction thereby intersecting the gate lines 121a and 121b. The data line 171 is connected to the first source electrode 173a extending toward the first gate electrode 124a and a second source electrode 173b extending toward the second gate electrode 124b. A first drain electrode 175a and a second drain electrode 175b are separated from the data line 171. The first drain electrode 175a faces the first source electrode 173a on the first gate electrode 124a, and the second drain electrode 175b faces the second source electrode 173b on the second gate electrode 124b.

In the shown exemplary embodiment, the first drain electrode 175a and the second drain electrode 175b include bar parts extending in a direction parallel to the data line 171. The drain electrodes 175a and 175b may have an expansion portion having a width that is widened from an end of the bar part of the drain electrodes 175a and 175b. The bar portion only represents a shape of the drain electrodes 175a and 175b according to one exemplary embodiment, and the present disclosure is not limited to the drain electrode 175a and 175b having the bar shape.

The thin film transistor including the first gate electrode 124a connected to the first gate line 121a, the first source electrode 173a, the first drain electrode 175a, and the first channel part 154a is connected to a pixel electrode 191 of the second pixel PX2. Similarly, the thin film transistor including the second gate electrode 124b connected to the second gate line 121b, the second source electrode 173b, the second drain electrode 175b, and the second channel part 154b is connected to the pixel electrode 191 of the third pixel PX3.

Semiconductor layers 151, 154a, and 154b may have substantially the same plane shape as the data conductors 171, 173a, 173b, 175a, and 175b and an underlying ohmic contact except for the channel region between the source electrodes 173a and 173b and the drain electrodes 175a and 175b. As one example, the data wire including the data line 171, the source electrodes 173a and 173b, and the drain electrodes 175a and 175b has a structure obtained by simultaneously forming the underlying ohmic contact (not shown) and the semiconductor layers 151, 154a, and 154b through one mask.

The first channel part 154a and the second channel part 154b of the semiconductor layer include a portion that is not covered but is exposed by the source electrodes 173a and 173b and the drain electrodes 175a and 175b between the source electrodes 173a and 173b and the drain electrodes 175a and 175b.

A passivation layer 180 is formed on the data wires 171, 173a, 173b, 175a, and 175b, and a first channel part 154a and a second channel part 154b of the exposed semiconductor layer. The passivation layer 180 is made of an inorganic insulator such as a silicon nitride and a silicon oxide. However, the passivation layer 180 may be made of an organic insulator and may provide a flat surface.

An organic layer 230 is positioned on the passivation layer 180. The organic layer 230 is mainly positioned in a region except for a position where the thin film transistor is formed. In the present exemplary embodiment, the organic layer 230 may extend in a column direction of the pixel electrode 191. The organic layer 230 may be a color filter, and the color filter may represent one of primary colors such as three primary colors of red, green, and blue. However, the color filter is not limited to the three primary colors of red, green, and blue, and may represent one of cyan, magenta, yellow, and white-based colors.

Figure 10:
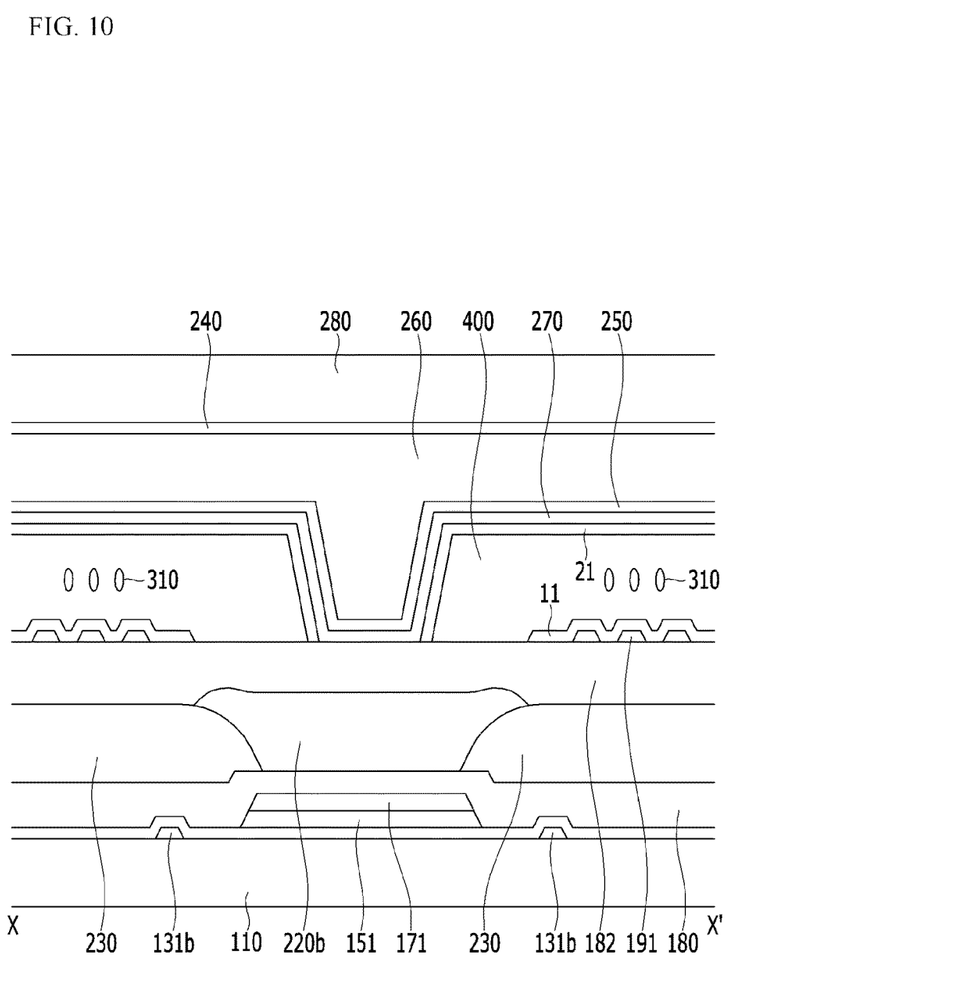
FIG. 10 is a cross-sectional view of the liquid crystal display of FIG. 9 taken along a line X-X'.

The neighboring organic layers 230 may be separated according to a horizontal direction D and a vertical direction crossing thereto as shown in FIG. 2, and the neighboring organic layers 230 are separated according to the horizontal direction in FIG. 10.

Referring to FIG. 10, a longitudinal light blocking member 220b is positioned between the organic layers 230 separated in the horizontal direction D. The longitudinal light blocking member 220b overlaps each edge of the neighboring organic layers 230, and widths of the longitudinal light blocking members 220b overlapping both edges of the organic layers 230 are substantially the same. The longitudinal light blocking member 220b is referred to as a black matrix and prevents light leakage. The longitudinal light blocking member 220b may be omitted, and in such case, the data line 171 may perform the light blocking member function.

A planarization layer 182 is formed on the longitudinal light blocking member 220b and the organic layer 230. The planarization layer 182 may be made of an organic material and may have a function of flattening the underlying layers.

The pixel electrode 191 is positioned on the planarization layer 182. The pixel electrode 191 is electrically connected to the drain electrodes 175a and 175b as one terminal of the thin film transistor through a contact hole 185. In detail, the pixel electrode 191 of the second pixel PX2 is connected to the first drain electrode 175a, and the pixel electrode 191 of the third pixel PX3 is connected to the second drain electrode 175b.

Referring to FIG. 9, each pixel electrode 191 may be formed as a fine slit electrode, and the overall shape of the fine slit electrode is a quadrangle and includes a crossed-shape stem that is configured of a transverse stem 191a and a longitudinal stem 191b intersecting the transverse stem 191a. Further, the pixel electrode 191 includes four subregions divided by the transverse stem 191a and the longitudinal stem 191b, and each sub-region includes a plurality of fine branch portions 191c.

One of the fine branch portions 191c of the fine slit electrode obliquely extends to the upper left from the transverse stem 191a or the longitudinal stem 191b, and another fine branch portion 191c obliquely extends to the upper right from the transverse stem 191a or the longitudinal stem 191b. A further fine branch portion 191c extends to the lower left from the transverse stem portion 191a or the longitudinal stem portion 191b, and still another fine branch portion 191c obliquely extends to the lower right from the transverse stem 191a or the longitudinal stem 191b. The fine branch portions 191c of two adjacent sub-regions may be orthogonal to each other. Although not illustrated, a width of the fine branch portion 191c may become gradually wider.

The bar portion of the described drain electrodes 175a and 175b is elongated according to the longitudinal stem 191b of the pixel electrode 191.

In the present exemplary embodiment, the passivation layer 180, the organic layer 230, and the planarization layer 182 have the contact hole 185, and the drain electrodes 175a and 175b and the pixel electrode 191 are connected to each other through the contact hole 185. In the present exemplary embodiment, the contact hole 185 may be formed at the crossing position of the transverse stem 191a and the longitudinal stem 191b of the pixel electrode 191. As shown in FIG. 9, the wide ends of the drain electrodes 175a and 175b overlap the crossing position of the transverse stem 191a and the longitudinal stem 191b, and the contact hole 185 is formed at this position.

In the subregions neighboring each other, directions in which the liquid crystal molecules are inclined are different from each other. The transverse stem 191a and the longitudinal stem 191b correspond to a boundary region where the neighboring subregions meet each other, and this boundary region corresponds to a non-transmission portion where the inclination direction of the liquid crystal molecules is not determined. Accordingly, in an exemplary embodiment of the present disclosure, although the drain electrodes 175a and 175b and the contact hole 185 are positioned within the pixel area PX, a decrease of the aperture ratio may be minimized.

A microcavity layer 400 is formed on the pixel electrode 191. The microcavity layer 400 is injected with a liquid crystal material including liquid crystal molecules 310, and the microcavity layer 400 has an inlet part (not shown). The microcavity layer 400 may be formed according to the column direction of the pixel electrode 191, in other words, the vertical direction.

A lower alignment layer 11 may be formed on the pixel electrode 191, and an upper alignment layer 21 may be formed on the microcavity layer 400. In this case, although not shown in FIG. 10, the lower alignment layer 11 and the upper alignment layer 21 may be realized to be connected to each other on the side.

In the present exemplary embodiment, an alignment material forming the alignment layers 11 and 21 and a liquid crystal material including the liquid crystal molecules 310 may be injected into the microcavity layer 400 by using capillary force.

A common electrode 270 and an overcoat 250 are positioned on the microcavity layer 400. The common electrode 270 receives a common voltage and generates an electric field along with the pixel electrode 191 applied with the data voltage to determine the inclination direction of the liquid crystal molecules 310 positioned in the microcavity layer 400 between the two electrodes. The common electrode 270 forms a capacitor along with the pixel electrode 191 such that an applied voltage is maintained after the thin film transistor is turned off. The overcoat 250 may be formed of a silicon nitride (SiNx) or a silicon oxide (SiOx).

A supporting member 260 is formed on the overcoat 250. The supporting member 260 may include silicon oxycarbide (SiOC), a photoresist, or other organic materials. When the supporting member 260 includes the silicon oxycarbide (SiOC), the supporting member 260 may be formed by a chemical vapor deposition method, and when including the photoresist, the supporting member 260 may be formed by a coating method. The silicon oxycarbide (SiOC) generally has a high transmittance and low layer stress, thereby not generating a change among layers that may be formed by the chemical vapor deposition method. Accordingly, in the present exemplary embodiment, by forming the supporting member 260 of the silicon oxycarbide (SiOC), light may be well transmitted, and a stable layer may be formed.

A protecting layer 240 is positioned on the supporting member 260. The protecting layer 240 may be made of a silicon nitride (SiNx) or a silicon oxide (SiOx). A capping layer 280 is positioned on the protecting layer 240. The capping layer 280 contacts the upper surface and the side wall of the supporting member 260, and the capping layer 280 covers liquid crystal injection holes not shown of the microcavity layer 400. The capping film 280 may be formed of a thermosetting resin, silicon oxycarbide (SiOC), or graphene.

When the capping film 280 is formed of graphene, the graphene has strong impermeability against a gas including helium and the like, and therefore may serve as the capping film blocking the liquid crystal injection holes A1 and A2, and is a material formed of carbon bonds such that it prevents the liquid crystal material from being contaminated even when contacting the capping film 280. In addition, the graphene may serve to protect the liquid crystal material from external oxygen and moisture.

While the present disclosure contains a detailed description of exemplary embodiments, the present disclosure is not limited to the disclosed embodiments. On the contrary, the present disclosure is intended to cover various modifications and equivalent arrangements included within the spirit and scope of the appended claims.

<Description of symbols>

| | |
|---|---|
| 1: wearable display device | 10: display unit |
| 100: output section | 101: user input section |
| 102: processor | 1021: wearing means adjustment section |
| 1023: certification section | 103: memory |
| 104: wired and wireless communication section | 105: power section |
| 20: wearing means | 201: sensor |
| 203: motor | |

What is claimed is:

1. A wearable display device comprising:
a display unit configured to display an image;
a wearing band configured to fix the display unit on a body part;
a plurality of sensors positioned on one surface of the wearing band and configured to contact a measuring target to measure at least one bio-signal from the measuring target;
a wearing band adjustment section included in the display unit and configured to adjust a length of the wearing band contacting the measuring target of the wearing band by using the at least one bio-signal,
a memory configured to store at least one information which directly or indirectly expresses the at least one bio-signal, and
a certification section configured to derive at least one of user certification information on the basis of the at least one bio-signal and store the at least one of user certification information in the memory,
wherein at least some of the plurality of sensors are configured to sense a first bio-signal generated by a user gesture,
the wearing band adjustment section compares the first bio-signal with a wear reference value stored in the memory to determine the length of the wearing band,
at least some of the plurality of sensors are configured to measure a second bio-signal from the measuring target,
the certification section is configured to derive the at least one of user certification information on the basis of the second bio-signal, and
the user certification information includes at least one selected from a wrist thickness and a wrist length of the measuring target when the wearable display device is worn on a wrist of the measuring target.

2. The wearable display device of claim 1, wherein
at least some of the plurality of sensors are configured to measure the second bio-signals at different positions with a predetermined interval between the different positions for the measuring target on the basis of the user gesture, and
the certification section is configured to derive at least one selected from the wrist thickness and the wrist length of the measuring target on the basis of the second bio-signals at the different positions.

3. The wearable display device of claim 1, wherein
at least some of the plurality of sensors are configured to measure a third bio-signal from the measuring target in a state in which the length of the wearing band is adjusted, and
the certification section is configured to perform a user certification procedure by determining whether the third bio-signal corresponds to the user certification information stored in the memory.

4. A method for controlling a wearable display device including a display unit, a wearing band fixing the display unit on a body part, a plurality of sensors contacting a measuring target and measuring at least one bio-signal from the measuring target, and a motor driven for length adjustment of the wearing band, the method comprising:
measuring a first bio-signal by at least some of the plurality of sensors, the first bio-signal generated in response to the wearable display device being worn on the body part;
adjusting a length of the wearing band contacting the measuring target of the wearing band on the basis of the first bio-signal;
measuring a second bio-signal from the measuring target by at least some of the plurality of sensors;
deriving at least one of a user certification information on the basis of the second bio-signal;
storing the at least one of user certification information in a memory;
using the user certification information to certify a user corresponding to the user certification information;
when the user is certified, providing a user interface according to a setting information of the display device for the user with reference to the memory, and
when the user is not certified, controlling the display unit so as to end a device operation in the display device;
wherein the step of adjusting the length of the wearing band includes:
comparing the first bio-signal and a predetermined wear reference value stored in the memory to determine the length of the wearing band;
generating a control signal including a signal on the length of the wearing band and transmitting the control signal to the motor by the display unit; and driving the motor to adjust the length of the wearing band on the basis of the control signal, and wherein the user certification information includes at least one selected from a wrist thickness and a wrist length information of the measuring target when the wearable display device is worn on a wrist of the measuring target.

5. The method of claim 4, wherein the step of storing the user certification information includes:

measuring the second bio-signals at different positions with a predetermined interval between the different positions for the measuring target depending on the user gesture by the at least some the plurality of sensors; and deriving at least one selected from the wrist thickness and the wrist length information of the measuring target on the basis of the second bio-signals at the different positions.

6. The method of claim 5, further comprising:

adjusting the length of the wearing band after storing the user certification information;

measuring a third bio-signal from the measuring target by the at least some of the plurality of sensors in a state in which the length of the wearing band is adjusted; and determining whether the third bio-signal corresponds to the user certification information stored in the memory to perform a user certification procedure.

7. The method of claim 6, wherein in the user certification procedure, the user certification procedure is performed by considering a predetermined error range when comparing the third bio-signal and the user certification information stored in the memory.

8. The method of claim 6, further comprising when the user certification procedure corresponds to a predetermined certification number, registering the wearable display device as a lost device.

* * * * *